United States Patent [19]

Masuhara et al.

[11] Patent Number: 4,746,685

[45] Date of Patent: May 24, 1988

[54] LIGHT CURABLE DENTAL COMPOSITION

[75] Inventors: Eiichi Masuhara; Yoshinori Kadoma, both of Tokyo; Takeo Matsumoto, Ibaragi; Takeshi Komai, Aichi; Eiichi Yamada, Ibaragi; Osamu Nakachi, Yokohama; Godo Irukayama, Ibaragi, all of Japan

[73] Assignee: Nippon Oil and Fats Co., Ltd., Tokyo, Japan

[21] Appl. No.: 768,546

[22] Filed: Aug. 23, 1985

[30] Foreign Application Priority Data

Aug. 31, 1984 [JP] Japan .................. 59-180268
Dec. 29, 1984 [JP] Japan .................. 59-275895
Feb. 26, 1985 [JP] Japan .................. 60-35342

[51] Int. Cl.$^4$ .................... A61K 6/08; C08F 2/50; C08F 4/14; C08F 4/36
[52] U.S. Cl. ........................ 522/13; 522/8; 522/120; 522/121; 522/77; 522/24; 522/46; 523/116; 526/320; 433/228.1
[58] Field of Search ............ 522/24, 8, 120, 121

[56] References Cited

U.S. PATENT DOCUMENTS

| | | | |
|---|---|---|---|
| 4,416,826 | 11/1983 | Neckers | 260/453 RZ |
| 4,459,193 | 7/1984 | Ratcliffe | 522/24 |
| 4,474,868 | 10/1984 | Yamaoka | 522/24 |
| 4,525,232 | 6/1985 | Rooney | 522/24 |
| 4,533,446 | 8/1985 | Conway | 522/24 |

FOREIGN PATENT DOCUMENTS 197401 11/1984 Japan .

OTHER PUBLICATIONS

Ishimaru "Photosensitive—" Chemical Abstracts vol. 91, No. 10, Abstract No. 81587a, 1979.
Hitachi (Ishimaru) "Photosensitive—" Derwent Abstract 79-28693 B/15, 1979.
Chimia Y Technologia, vol. 6, 1980, pp. 23–25.
Komai, J59-197401 of Nov. 9, 1984, Japio Abstract No. 84-197401.
Komai, EP-126541-A of 28 Nov. 1984, Derwent Abstract No. 84-295941/48.

*Primary Examiner*—John C. Bleutge
*Assistant Examiner*—A. H. Koeckert
*Attorney, Agent, or Firm*—Jordan and Hamburg

[57] ABSTRACT

A light curable dental composition is provided. The composition comprises an ethylenic unsaturated compound and a light polymerization initiator. The light polymerization initiator is selected from a combination of an organic peroxide and a pyrylium salt compound of:

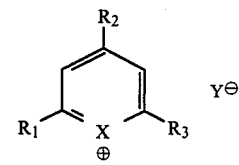

Wherein $R_1$, $R_2$, and $R_3$ each represents a hydrogen atom, an alkyl group and the like, X stands for an oxygen or sulfur atom and Y for an anionic functional group; a polyperoxy ester containing a benzophenone group; and a combination the polyperoxy ester and an α-diketone.

16 Claims, No Drawings

LIGHT CURABLE DENTAL COMPOSITION

BACKGROUND OF THE INVENTION

1. Field of the Invention

The present invention relates generally to a light curable dental composition, and more particularly to a dental composition which can be cured by irradiation of light to be utilized for teeth crown materials, denture base materials, dental cementing materials, dental bonding materials, dental filling materials, dental impression materials and caries-preventive materials.

2. Related Art Statements

Heat-polymerizable dental compositions wherein organic peroxides, such as benzoyl peroxide, are used as the polymerization initiators and cold-setting type dental compositions wherein Redox type polymerization initiators, such as a combination of benzoyl peroxide with a tertiary amine, are used as the polymerization initiators have been known in the art. Further known in the art is a composition containing a sensitizer such as benzoin alkyl ether to be cured by irradiation of ultraviolet rays.

However, the known heat-polymerizable and cold-setting type dental compositions have a disadvantage that the cured resins tend to contain air bubbles to lower the mechanical strengths and water-proof properties, since they are prepared by mixing a powder with a liquid or kneading a paste with another paste. In addition, the heat-polymerizable dental compositions have another disadvantage that a complicate and time-consuming operation is required for polymerization. On the other hand, the cold-setting type dental compositions have additional disadvantages that the curing speed thereof is too high to cause difficulties in clinical operation, and that the formed denture is colored to deteriorate the appearance due to the undesirous action by the tertiary amine.

The composition containing an ordinary light polymerization initiator sensitive to ultraviolet rays, such as benzoin alkyl ether, gives rise to problems that the transmittance to ultraviolet rays effective to polymerization or curing is so low as to limit the depth of cured composition only to less than 2 mm resulting in unsatisfactory curing depth, that a filter or other protection means is indispensable since the ultraviolet rays contain the rays having wavelengths of less than 320 nm which are harmful to human being, and that the lifetime of a mercury lamp used as the irradiation source is short so that the lamp is damaged soon.

Further known in the art is an one-paste type dental composition containing a light polymerization initiator. However, the known dental composition of this type has disadvantages that the mechanical strengths, particularly the bending strength, of the cured product is low, and that it is inferior in handling ease or operation facility when used in practical operation.

OBJECTS AND SUMMARY OF THE INVENTION

A primary object of this invention is to provide a light curable dental composition which can be readily cured by irradiation of light within a short time period to give a cured product which is set deep in the interior region thereof.

Another object of this invention is to provide a light curable dental composition which is inexpensive and excellent in curing property, and yet ensures safe and easy operation in clinical application.

A further object of this invention is to provide a light curable dental composition which forms a colorless cured product of clear appearance.

A still further object of this invention is to provide a light curable dental composition which has a surface of lower adhesiveness to make the handling in clinical operation easier and forms a cured product having higher mechanical strengths including the bending strength.

The above and other objects of the invention will become apparent from the following description.

A light curable dental composition provided in accordance with the present invention comprises an ethylenic unsaturated compound and a light polymerization initiator, said light polymerization initiator being selected from the group consisting of:

(a) a combination of an organic peroxide and a pyrylium salt compound represented by the following general formula [I] of:

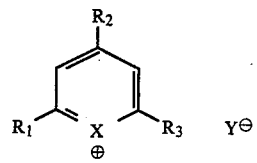

wherein $R_1$, $R_2$ and $R_3$ each represents the same or different atom or group and stands for a hydrogen atom, a halogen atom, an alkyl group, a haloalkyl group, an ethylenyl group, a styryl group, an alkoxy group, a phenyl group, a naphthyl group, an alkylphenyl group, an alkoxyphenyl group, a hydroxyphenyl group, a halophenyl group, a nitrophenyl group, an aminophenyl group, an alkylaminophenyl group, an alkylaminostyryl group, a nitro group, an amino group or a hydroxyl group, X stands for an oxygen atom or a sulfur atom and Y for an anionic functional group;

(b) a polyperoxy ester containing a benzophenone group and represented by the following general formula [II] of:

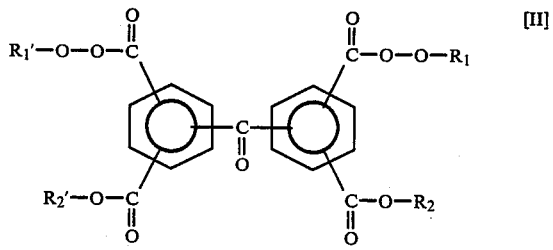

wherein $R_1$ and $R_1'$ each represents the same or different group and stands for a tertiary alkyl group having 4 to 8 carbon atoms or a tertiary aralkyl group having 9 to 12 carbon atoms and $R_2$ and $R_2'$ each represents the same or different atom or group and stands for a hydrogen atom, a tertiary alkoxy group having 4 to 8 carbon atoms or a tertiary aralkyloxy group having 9 to 12 carbon atoms; and (c) a combination of said polyperoxy ester represented by the general formula [II] and an α-diketone.

DESCRIPTION OF THE INVENTION

The present invention will be described in detail hereinbelow.

The light curable dental composition, according to the invention, comprises an ethylenic unsaturated compound and one or more of specific light polymerization initiators.

Any ethylenic unsaturated compounds which have been conventionally used in the dental compositions may be used conveniently in the composition of the invention, the examples being derivatives of methacrylic acid, such as methyl methacrylate, 2-hydroxyethyl methacrylate, neopentylglycol dimethacrylate, 1,4-butanediol dimethacrylate, ethyleneglycol dimethacrylate, diethyleneglycol dimethacrylate, triethyleneglycol dimethacrylate, polyethyleneglycol dimethacrylate, propyleneglycol dimethacrylate, dipropyleneglycol dimethacrylate, tripropyleneglycol dimethacrylate, polypropyleneglycol dimethacrylate, tetromethylolmethane trimethacrylate, tetramethylolmethane tetramethacrylate, hexamethyleneglycol dimethacrylate, 2,2-bis(4-methacryloxyphenyl)propane, 2,2-bis(4-methacryloxyethoxyphenyl)propane, 2,2-bis(4-methacryloxypolyethoxyphenyl)propane, 2,2-bis[4-(3-methacryloxy-2-hydroxypropoxy)phenyl]propane, 1,2-bis(3-methacryloxy-2-hydroxypropoxy)ethane, 2,2-bis(4-methacryloxyphenyl)propane, 2-hydroxy-1,3-dimethacryloxypropane, di-2-methacryloxyethyl-2,2,4-trimethylhexamethylene dicarbamate, 2-hydroxy-3-phenoxypropyl methacrylate, 2-hydroxy-3-p-t-butylphenoxypropyl methacrylate, methacryloxyethylphenylphospholic acid, 4-methacryloxyethyl trimellitate anhydride and mixtures thereof. Other derivatives of acrylic acid, styrene and derivatives of styrene may also be used in the present invention. Curable resins having maleate, fumarate, allyl or (meth)acrylate groups, unsaturated polyester resins, unsaturated acrylic resins, or acrylate oligomers modified with isocyanate, polyester-acryl oligomers, polyether-acryl oligomers, etc. may be used in the present invention.

The specific light polymerization initiator which may be used in the invention is selected from the group consisting of:

(a) a combination of an organic peroxide and a pyrylium salt compound represented by the following general formula [I] of:

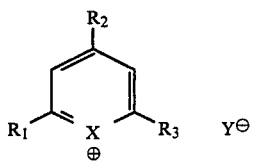

wherein $R_1$, $R_2$ and $R_3$ each represents the same or different atom or group and stands for a hydrogen atom, a halogen atom, an alkyl group, a haloalkyl group, an ethylenyl group, a styryl group, an alkoxy group, a phenyl group, a naphthyl group, an alkylphenyl group, an alkoxyphenyl group, a hydroxyphenyl group, a halophenyl group, a nitrophenyl group, an aminophenyl group, an alkylaminophenyl group, an alkylaminostyryl group, a nitro group, an amino group or a hydroxyl group, X stands for an oxygen atom or a sulfur atom and Y for an anionic functional group;

(b) a polyperoxy ester containing a benzophenone group and represented by the following general formula [II] of:

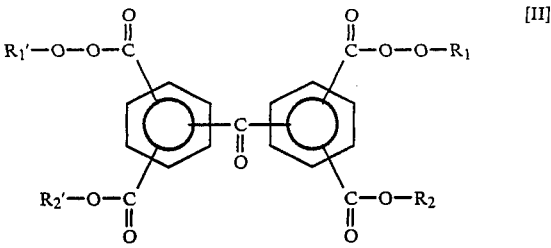

wherein $R_1$ and $R_1'$ each represents the same or different group and stands for a tertiary alkyl group having 4 to 8 carbon atoms or a tertiary aralkyl group having 9 to 12 carbon atoms and $R_2$ and $R_2'$ each represents the same or different atom or group and stands for a hydrogen atom, a tertiary alkoxy group having 4 to 8 carbon atoms or a tertiary aralkyloxy group having 9 to 12 carbon atoms; and (c) a combination of the polyperoxy ester represented by the general formula [II] and an α-diketone.

Initially, the light polymerization initiator which is the combination of an organic peroxide and a pyrylium salt compound represented by the aforementioned general formula [I] will be described.

A single or a combination of two or more organic peroxides, each having one or more oxygen-oxygen bonds in one molecule, may be used in the invention, the specific examples being methyl ethyl ketone peroxide, cyclohexanone peroxide, acetylacetone peroxide, 1,1-bis(t-butylperoxy)cyclohexane, t-butylhydroperoxide, cumene hydroperoxide, diisopropylbenzene hydroperoxide, p-methane hydroperoxide, di-t-butyl peroxide, t-butylcumyl peroxide, dicumyl peroxide, 2,5-dimethyl-2,5-di(t-butylperoxy)hexane, acetyl peroxide, octanoyl peroxide, lauroyl peroxide, 3,5,5-trimethylhexanoyl peroxide, benzoyl peroxide, diisopropylperoxy dicarbonate, di-2-ethylhexylperoxy dicarbonate, di(3-methyl-3-methoxybutyl)peroxy dicarbonate, t-butylperoxy isobutylate, t-butylperoxy octanoate, t-butylperoxy benzoate, di-t-butyldiperoxy isophthalate, 2,5-dimethyl-2,5-di(benzoylperoxy)hexane, 3,3',4,4'-tetra(tertiarybutylperoxycarbonyl)benzophenone, tri(t-butylperoxy)trimellitate, 3,3',4,4'-tetra-(t-amylperoxycarbonyl)benzophenone, 3,3',4,4'-tetra-(t-hexylperoxycarbonyl)benzophenone, 3,3',4,4'-tetra-(t-octylperoxycarbonyl)benzophenone, 3,3',4,4'-tetra-(cumylperoxycarbonyl)benzophenone, 3,3',4,4'-tetra-(p-isopropylcumylperoxycarbonyl)benzophenone, and mixtures thereof.

A single or a combination of two or more pyrylium salt compounds may be used in the invention, and the examples of the pyrylium compound include pyrylium salts and thiopyrylium salts represented by the general formula [I] wherein the anionic functional group Y is perchlorate, fluoroborate, fluorophosphonate, fluoroantimonate, chloroaluminate, sulphuracetate, methosulfate, thiocyanate, sulfate, nitrate or acetate.

The specific examples of the compounds represented by the general formula [I] will be listed as follows:

4-(4-butoxyphenyl)-2,6-bis(4-methoxyphenyl)pyrylium fluoroborate, 4-(4-butoxyphenyl)-2,6-diphenylthiopyrylium fluoroborate, 4-(4-butoxyphenyl)-2,6-bis(4-methoxyphenyl)thiopyrylium fluoroborate,
2,6-bis(4-methoxyphenyl)-4-phenylthiopyrylium fluoroborate,
4-(4-butoxyphenyl)-2,6-diphenylpyrylium fluoroantimonate,
2-methyl-4,6-bis(4-methoxyphenyl)thiopyrylium fluoroborate,
2,4,6-tri(4-methoxyphenyl)thiopyrylium perchlorate,
2,4,6-tri(4-methoxyphenyl)thiopyrylium fluoroborate,
4-(3,4-diethoxyphenyl)-2,6-bis(4-methoxyphenyl)thiopyrylium fluoroborate,
4-(4-dimethylaminophenyl)-2,6-diphenylthiopyrylium perchlorate,
2-nitro-4,6-bis(4-dimethylaminostyryl)pyrylium fluoroborate,
2-methoxy-4-naphthyl-6-styrylthiopyrylium fluoroborate,
2-amino-4,6-bis(4-butoxyphenyl)thiopyrylium perchlorate,
2-(4-nitrophenyl)-4,6-bis(4-butylphenyl)thiopyrylium fluoroborate,
2-hydroxy-4,6-bis(4-dimethylaminostyryl)pyrylium perchlorate,
2-(3,4-dichlorophenyl)-4-(4-methoxyphenyl)-6-phenylpyrylium fluoroborate.

The pyrylium or thiopyrylium salt which acts as a sensitizer is contained in the composition preferably in an amount of 0.0001 to 1 part by weight, more preferably 0.001 to 0.5 part by weight, based on 100 parts by weight of the ethylenic unsaturated compound. If the content of the sensitizer is less than 0.0001 part by weight, the composition can not be cured by irradiation of visible ray; whereas the content of the sensitizer in excess of 1 part by weight is undesirable for the reason that the thickness of cured layer (i.e. the depth of curing) is conversely decreased and for hygienic reason.

Preferable content of the organic peroxide ranges within 0.001 to 10 parts by weight, more preferably within 0.01 to 5 parts by weight, based on 100 parts by weight of the ethylenic unsaturated compound. If the content of the organic peroxide is less than 0.001 part by weight, the composition is not curable, whereas the content thereof in excess of 10 parts by weight is undesirable because of the deterioration of the properties of the cured product.

When a combination of the organic peroxide and the sensitizer is used as the light polymerization initiator, the composition may be readily cured by irradiation of a visible ray having a wavelength of from 400 nm to 700 nm for a short time so that the depth of curing reaches not less than 5 mm to make the composition well adapted for dental uses.

The light polymerization initiator which is a polyperoxy ester containing a benzophenone group and represented by the aforementioned general formula [II] will now be described in detail. The polyperoxy esters represented by the general formula [II] wherein the carbon number in either of $R_1$ or $R_1'$ exceeds 9 are inferior in polymerization initiating function due to depression in active oxygen emission. Likewise, the polyperoxy esters represented by the general formula [II] wherein the carbon number in either of $R_2$ or $R_2'$ exceeds 13 are inferior in polymerization initiating function. A single or a combination of two or more polyperoxy esters containing a benzophenone group and represented by the general formula [II] may be used in the invention, and the specific examples thereof include 3,3',4,4'-tetra-(t-butylperoxycarbonyl)benzophenone, 3,3',4,4'-tetra-(t-amylperoxycarbonyl)benzophenone, 3,3',4,4'-tetra-(t-hexylperoxycarbonyl)benzophenone, 3,3',4,4'-tetra-(t-octylperoxycarbonyl)benzophenone, 3,3',4,4'-tetra-(cumylperoxycarbonyl)benzophenone, 3,3',4,4'-tetra-(p-isopropylcumylperoxycarbonyl)benzophenone, 3,3'-dicarboxy-4,4'-di(t-butylperoxycarbonyl)benzophenone, 3,3'-dicarboxy-4,4'-di(t-hexylperoxycarbonyl)benzophenone and mixtures thereof.

The concentration of the polyperoxy ester containing a benzophenone group and acting as a light polymerization initiator ranges preferably within 0.01 to 10 parts, more preferably within 0.05 to 5 parts, by weight, based on 100 parts by weight of the ethylenic unsaturated compound. If the concentration of the light polymerization initiator is less than 0.01 part by weight, the composition is not curable. On the contrary, if the concentration of the light polymerization initiator is more than 10 parts by weight, the properties of cured product are adversely deteriorated. When a polyperoxy ester containing a benzophenone group is used as the light polymerization initiator, the composition may be readily cured by irradiation of a harmless ray having a wavelength of from 350 nm to 450 nm within a short time period to form a colorless and beutiful cured product.

The light polymerization initiator which is a combination of the polyperoxy ester containing a benzophenone group and represented by the aforementioned general formula [II] and an α-diketone will now be described in detail. In this case, a single or a mixture of two or more polyperoxy esters each having a benzophenone group may be combined with a single or a mixture of two or more α-diketones. Any α-diketones may be used as far as they have a peak absorption at a wavelength of 400 nm to 700 nm, the specific examples being biacetyl, 2,3-pentadione, 2,3-octadione, bonzyl, 4,4'-dimethoxybenzyl, 4,4'-oxybenzyl, 4,4'-dichlorobenzyl, acenaphthenequinone, 9,10-phenanthrenequinone, camphorquinone and β-naphthoquinone. Any one or a mixture of the α-diketones may be used. Particularly preferred α-diketones are acenaphthenequinone, 9,10-phenanthrenequinone, camphorquinone and β-naphthoquinone.

The concentration of the α-diketone ranges preferably within 0.01 to 10 parts by weight, more preferably within 0.1 to 5 parts by weight, based on 100 parts by weight of the ethylenic unsaturated compound. If the concentration of α-diketone is less than 0.01 part by weight, no appreciable effect is provided by the addition of α-diketone. On the contrary, if the concentration of α-diketone is more than 10 parts by weight, not all of the added α-diketone is dissolved in the composition or the depth of curing is decreased, in addition to undesirable hygienic influence.

The concentration of the polyperoxy ester having a benzophenone group ranges preferably within 0.01 to 10 parts by weight, more preferably within 0.1 to 5 parts by weight, based on 100 parts by weight of the ethylenic unsaturated compound. If the concentration of the polyperoxy ester having a benzophenone group is less than 0.01 part by weight, no appreciable effect is provided by the addition of polyperoxy ester having a benzophenone group. On the contrary, if the concentration of the polyperoxy ester having a benzophenone group is more than 10 parts by weight, not all of the added polyperoxy ester is dissolved in the composition or the properties of the cured product are deteriorated, in addition to undesirable hygienic influence.

When a combination of the α-diketone and the polyperoxy ester having a benzophenone group is used as the light polymerization initiator, the composition may be readily cured by irradiation of a visible ray having a wavelength of from 400 nm to 700 nm for a short time period in a depth of curing of not less than 4 mm so that the composition can be well adapted for curable dental applications.

The light curable dental composition, according to the invention, may contain fine particles of inorganic filler with or without the addition of high polymer surface active agent. Preferable inorganic filler used for this purpose include apatite, soda-lime glass, silica, quartz, borosilicate glass, alumina, barium oxide, zirconium glass and mixtures thereof. A particularly preferred inorganic filler is a silica having an average particle size of from 1 to 100 millimicrons and being treated to be hydrophobic with a treating agent, such as dimethyldichlorosilane, hexamethyldisilazane, octyltrimethoxysilane or silicone oils, because such silica is improved in light transmittance, water-proof property and thixotropy.

High polymer surface active agents which may be added to the composition of the invention include copolymers each being prepared by copolymerizing an unsaturated monomer represented by the following general formula [III] of:

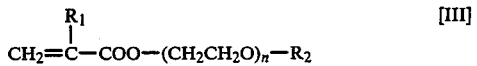

wherein
R₁ is a hydrogen atom or a methyl group,
R₂ is an alkyl group having 1 to 4 carbon atoms or a phenyl group, and n is an integer of 1 to 15;
with an unsaturated ester copolymerizable with the monomer represented by the general formula [III]. The copolymers prepared from unsaturated monomers represented by the general formula [III] wherein n exceeds 15 are noot preferred, since they become so hydrophilic as to have lower water-proof property of the product composition.

The specific examples of the unsaturated monomer represented by the general formula [III] are methoxyethyl (meth)acrylate, phenoxyethyloxyethyl (meth)acrylate, methoxydiethyleneglycol (meth)acrylate, methoxytetraethyleneglycol (meth)acrylate, isobutoxytetraethyleneglycol (meth)acrylate, methoxypolyethyleneglycol (meth)acrylate, ethoxypolyethyleneglycol (meth)acrylate, isopropoxypolyethyleneglycol (meth)acrylate, isobutoxypolyethyleneglycol (meth)acrylate, phenoxypolyethyleneglycol (meth)acrylate and mixtures thereof. In the specific examples listed above, "poly" means that n indicating the number of respective repeating unit ranges within 5 to 15.

Examples of the unsaturated ester copolymerizable with the aforementioned monomer [III] are (meth)acrylic esters such as methyl (meth)acrylate, ethyl (meth)acrylate, propyl (meth)acrylate, butyl (meth)acrylate and mixtures thereof.

The aforementioned copolymers may be prepared through ordinary solution polymerization, suspension polymerization or emulsion polymerization while using a radical polymerization initiator. The molecular weight of the copolymer ranges preferably from 10 to 500 thousands in consideration of solubility and lower adhesiveness.

The composition of the invention containing fine particles of an inorganic filler and a high polymer surface active agent selected from the copolymers listed above, may be conveniently used as a denture base material and as a dental impression material. It is desirous that 30 to 80 parts by weight of one or more of the ethylenic unsaturated compounds are mixed with 50 to 10 parts by weight of fine particles of one or more of the aforementioned inorganic fillers and 0.1 to 20 parts by weight of one or more of the aforementioned copolymers acting as effective surface active agents. The compositions outside of the aforementioned mixing range are inconvenient since they form sticky pastes or form pastes which are too low in viscosity to lose integrity for maintaining a stable shape, or eventually they cannot form pastes. The composition containing the dental filling material and the surface active agent, as aforementioned, provides a dental composition of paste form which has a pertinent viscosity and a low surface tackiness to be adapted for easy application in clinical operation, and is cured to form a cured mass having excellent mechanical strengths, particularly superior in bending strength.

Any of the dental compositions prepared in accordance with the present invention, irrespective of the particular light polymerization initiator selected from the group defined in the appended claims with or without the addition of the fine particles of any one or more inorganic fillers and high polymer surface active agents, may be further added with an additional dental filling material which has been ordinarily used in dental application. Examples of such a dental filling material are apatite, soda-lime glass, silica, quartz, silica gel, borosilicate glass, synthetic sapphire (alumina) and radioactive opaque filling materials, such as barium oxide and zirconium glass. The dental filling material may be in the form of beads, micro-powders, micro-plates, fibers or whiskers, or may have irregular shapes. In addition to the aforementioned ingredients, an appropriate amount of other dental additives, such as binder resin, polymerization inhibitor, antioxidant, stabilizer, pigment, dye or viscosity increasing agent, may be added, as desired.

The dental composition of the invention may be mixed by a manufacturer, charged in a sealed container in the form of a composite liquid or paste, and supplied to a dentist or a dental technician. A dentist or dental technician may apply or fill the dental composition of the invention thus supplied to mold the same, and then the composition is irradiated by a light from an irradiation source to be polymerized and cured.

Any irradiation sources may be used for curing the composition of the invention as far as they generate lights having wavelengths within the aforementioned range, examples being a xenon lamp, a halogen lamp, a tungsten lamp, a fluorescent lamp, a metal halide lamp and a laser.

The dental composition of the invention can be cured readily by irradiation of light within a short time period to be cured deeper in the interior region and is superior over the conventional composition using a polymerization initiator sensitive to ultraviolet rays. The dental composition of the invention is further improved in safe and easy handling in clinical operation and in economical viewpoint.

EXAMPLES OF THE INVENTION ventional sensitizer sensitive to ultraviolet rays was not cured by exposure to visible light irradiation.

TABLE 1

|  | Ethylenic Unsaturated Compound[*1] (part by wt.) | Organic Peroxide[*2] (part by wt.) | Sensitizer[*3] (part by wt.) | Exposure Time (sec) | Depth of Curing (mm) |
| --- | --- | --- | --- | --- | --- |
| Example 1 | 3G 100 | LPO 1.0 | BMTF 0.010 | 20 | 7.2 |
| Example 2 | 3G 100 | BPO 1.0 | BMPF 0.010 | 30 | 5.0 |
| Example 3 | 3G 100 | PBIF 2.0 | BMTF 0.010 | 35 | 6.5 |
| Example 4 | 3G 100 | TBB 2.0 | BMPF 0.010 | 40 | 6.5 |
| Example 5 | 3G 50 & bis-GMA 50 | PBIF 1.5 | BMTF 0.012 | 30 | 6.3 |
| Example 6 | 3G 50 & bis-GMA 50 | TBB 2.0 | BMTF 0.005 | 20 | 7.5 |
| Example 7 | 3G 50 & bis-GMA 50 | PH25Z 2.0 | BMTF 0.010 | 35 | 6.2 |
| Example 8 | bis-GMA 50 & UDMA 50 | TBB 1.5 | MPTF 0.010 | 20 | 7.3 |
| Example 9 | bis-GMA 50 & HMDA 50 | PBIF 2.0 | APTP 0.005 | 30 | 6.3 |
| Example 10 | HDMP 100 | TBB 1.0 | BPPA 0.020 | 30 | 6.4 |

Note:
[*1]3G: Triethylenglycol Dimethacrylate
bis-GMA: 2,2-Bis[4-3-methacryloxy-2-hydroxypropoxy)phenyl]propane
UDMA: Di-2-methacryloxyethyl-2,2-4-trimethylhexamethylene Dicarbamate
HMDA: Hexamethyleneglycol Dimethacrylate
HDMP: 1,2-Bis(3-methacryloxy-2-hydroxypropoxy)ethane
[*2]LPO: Lauroyl Peroxide
BPO: Benzoyl Peroxide
PBIF: Di-t-butyldiperoxy Isophthalate
TBB: 3,3',4,4'-Tetra(t-butylperoxycarbonyl) Benzophenone
PH25Z: 2,5-Dimethyl-2-5-di(benzoylperoxy)hexane
[*3]BMTF: 4-(4-Butoxyphenyl)-2,6-bis(4-methoxyphenyl)thiopyrylium Fluoroborate
BMPF: 4-(4-Butoxyphenyl)-2,6-bis(4-methoxyphenyl) pyrilium Fluoroborate
MPTF: 2,6-Bis(4-methoxyphenyl)-4-phenylthiopyrilium Fluoroborate
APTP: 4-(4-Dimethylaminophenyl)-2,6-diphenylthiopyrylium Perchlorate
BPPA: 4-(4-Butoxyphenyl)-2,6-diphenylpyrylium Fluoroantimonate The present invention will now be described more specifically by referring to examples and comparative examples. It should be noted here that the following examples are given by way of example only, and the present invention is not limited thereby.

EXAMPLES 1 TO 10

Each of the compositions, as set forth in Table 1, was prepared by dissolving the organic peroxide and the sensitizer in the ethylenic unsaturated compound. The composition was filled in a polyethylene cylinder having an inner diameter of 10 mm and a depth of 10 mm, and exposed to visible light ray irradiation from a halogen lamp (150 watts, Maximum Irradiation Wavelength: 490 nm) placed above the cylinder by 3 mm to be polymerized and cured. The depth of curing of each composition was measured using a micrometer after the polymerized and cured mass was recovered from the cylinder and the unreacted material was removed therefrom. The results are shown in Table 1.

As should be appreciated from the results set forth in Table 1, the dental compositions of the invention were cured deep in the interior region (to have a depth of curing of not less than 5 mm) by exposure to visible lights for a short time period of about 20 to 40 seconds to be adapted for use as excellent teeth crown materials, denture base materials, dental cementing repair materials and dental impression materials while being improved in handling ease in clinical operation.

COMPARATIVE EXAMPLE 1

A test sample was prepared by using 100 parts by weight of triethyleneglycol dimethacrylate as the ethylenic unsaturated compound, 2.0 parts by weight of di-t-butylperoxy isophthalate as the organic peroxide, and 0.5 part by weight of benzoinisobutyl ether as the sensitizer without the addition of a pyrylium salt compound. The other procedures were similar to Examples 1 to 10. The test sample was not cured after being exposed to light irradiation for 180 seconds, after all. The result revealed that the composition containing a con-

EXAMPLES 11 to 20

Each of the compositions, as set forth in Table 2, was prepared by dissolving the light polymerization initiator in the ethylenic unsaturated compound to prepare a dental composition. The composition was filled in a polyethylene cylinder having an inner diameter of 10 mm and a depth of 10 mm, and exposed to light ray irradiation from a halogen lamp (15 volts, 150 watts) placed above the cylinder by 3 mm, while filtering off the light rays having wavelengths of less than 350 nm, to be polymerized and cured. The depth of curing of each composition was measured using a micrometer after the polymerized and cured mass was recovered from the cylinder and the unreacted material was removed therefrom. The results are shown in Table 2.

EXAMPLES 21 AND 22

Each of the compositions, as set forth in Table 2, was prepared by dissolving the light polymerization initiator uniformly in the ethylenic unsaturated compound, followed by adding a silica gel base filler (AEROSIL R 972 produced by Aerosil Nippon K.K.), and then kneaded by twin rollers to obtain a dental composition. The depth of curing was measured generally following the procedures as conducted in Examples 11 to 20. The results are shown in Table 2.

As should be appreciated from the results set forth in Table 2, the dental compositions of the invention were cured deep in the interior region (to have a depth of curing of not less than 5 mm) by exposure to lights deprived of those having the wavelengths of less than 350 nm for a short time period of about 30 to 60 seconds to be adapted for use as excellent teeth crown materials, denture base materials, dental cementing repair materials, caries-preventive materials and dental impression materials while being improved in handling ease in clinical operation and having good appearance without coloring.

COMPARATIVE EXAMPLES 2 and 3

Similar tests, as in Examples 11 to 20, were conducted while using triethyleneglycol dimethacrylate as the ethylenic unsaturated compound which was added with the polymerization initiators as set forth in Table 3.

As will be seen from the results set forth in Table 3, the composition containing conventional light polymerization initiators sensitive to ultraviolet rays are not curable even when they are exposed to light rays deprived of the light fractions having the wavelengths of less than 350 nm.

each composition was measured using a micrometer after the polymerized and cured mass was recovered from the cylinder and the unreacted material was removed therefrom. The results are shown in Table 4.

As should be appreciated from the results set forth in Table 4, the dental compositions of the invention were cured deep in the interior region (to have a depth of curing of not less than 5 mm) by exposure to visible lights for a short time period of about 20 to 40 seconds. It should be also apparent from the results irradiated by light rays passing through color glass filters that the compositions of the invention can be effectively cured

TABLE 2

| | Ethylenic Unsaturated Compound*[1] (part by wt.) | Light Polymerization Initiator*[2] (part by wt.) | Filler (part by wt.) | Exposure Time (sec) | Depth of Curing (mm) | Color of Cured Mass |
| --- | --- | --- | --- | --- | --- | --- |
| Example 11 | 3G 100 | TBB 1.0 | — | 30 | 5.0 | colorless |
| Example 12 | 3G 100 | TAB 1.0 | — | 40 | 6.0 | colorless |
| Example 13 | 3G 100 | THB 1.0 | — | 50 | 6.5 | colorless |
| Example 14 | 3G 100 | TOB 1.0 | — | 60 | 7.1 | colorless |
| Example 15 | 3G 100 | TCB 1.5 | — | 40 | 5.5 | colorless |
| Example 16 | 3G 100 | TIB 2.0 | — | 40 | 5.8 | colorless |
| Example 17 | 3G 50 & bis-MEPP 50 | TBB 1.0 & THB 0.2 | — | 30 | 5.1 | colorless |
| Example 18 | HMDA 50 & UDMA 50 | TBB 1.0 & CBP 0.1 | — | 40 | 6.1 | colorless |
| Example 19 | TMM-3M 50 & HDMP 50 | TBB 1.0 & CHP 0.1 | — | 50 | 6.6 | colorless |
| Example 20 | 3G 50 & bis-GMA 50 | TBB 0.5 | — | 60 | 7.2 | colorless |
| Example 21 | 3G 25 & bis-GMA 25 | TBB 1.5 | 40 | 60 | 6.5 | colorless |
| Example 22 | 3G 20 & bis-GMA 30 | TBB 1.5 | 50 | 60 | 6.4 | colorless |

Note:
*[1]bis-MEPP: 2,2-Bis(4-methacryloxyethoxyphenyl)propane
TMM-3M: Tetramethylolmethane Trimethacrylate
The other abridged notations are the same as noted in the note of Table 1.
*[2]TBB: 3,3',4,4'-Tetra-(t-butylperoxycarbonyl)benzophenone
TAB: 3,3',4,4'-Tetra-(t-amylperoxycarbonyl)benzophenone
THB: e,e',4,4'-Tetra-(t-hexylperoxycarbonyl)benzophenone
TOB: 3,3',4,4'-Tetra-(t-octylperoxycarbonyl)benzophenone
TCB: 3,3',4,4'-Tetra-(cumylperoxycarbonyl)benzophenone
TIB: e,e',4,4'-Tetra-(p-iso ro ylcumylperoxycarbonyl)benzophenone
CBP: 3,3'-Dicarboxy-4,4'-di(t-butylperoxycarbonyl)benzophenone
CHP: 3,3'Dicarboxy-4,4'-di(t-hexylperoxycarbonyl)benzophenone

TABLE 3

| | Ethylenic Unsaturated Compound (part by wt.) | Light Polymerization Initiator (part by wt.) | Exposure Time (sec) | Depth of Curing (mm) |
| --- | --- | --- | --- | --- |
| Comparative Example 2 | 3G 100 | BF* 1.0 | 60 | 0 |
| Comparative Example 3 | 3G 100 | BIE** 1.0 | 60 | 0 |

Note:
*BF: Benzophenone
BIE: Benzoinisobutyl Ether
The other abridged notations are the same as noted in the Note of Table 1.

EXAMPLES 23 TO 34

Each of the compositions, as set forth in Table 4, was prepared by dissolving the α-diketone and the polyperoxy ester containing a benzophenone group uniformly in the ethylenic unsaturated compound. The composition was filled in a polyethylene cylinder having an inner diameter of 10 mm and a depth of 10 mm, and exposed to visible light ray irradiation from a halogen lamp (15 volts, 150 watts) placed above the cylinder by 3 mm to be polymerized and cured. In order to learn the precise effect of irradiated light wavelength, the top of the cylinder filled with the composition was covered with a color glass filter through which the visible light rays from the halogen lamp was irradiated. The used color glass filters were Y-43 and Y-47 (produced by Toshiba Co., Ltd.) which had, respectively, the limit transmission wavelengths of 430 nm and 470 nm. The light intensity passing through the color glass filter was reduced to about one half to one third of the intensity of light emitted from the lamp. The depth of curing of by extremely safe light rays having the wavelengths of not less than 470 nm although the intensity of light rays passing through the filters is lowered to one half to one third of the light intensity originally emitted from the lamp. As will be understood from the foregoing, the dental compositions prepared in accordance with the present invention have superior properties when used as teeth crown materials, denture base materials, dental cementing repair materials and dental impression materials while being improved in handling ease and safety in clinical operation.

COMPARATIVE EXAMPLES 4 TO 7

Each test sample was prepared by mixing the components in the ratio as set forth in Table 5, and subjected to tests conducted similarly as in the precedng Examples. As will be seen from the results shown in Table 5, a composition merely containing an α-diketone or containing a combination of an α-diketones with an ordinary organic peroxide cannot be cured by visile light rays to a satisfactory curing level.

TABLE 4

|  | Ethylenic Unsaturated Compound*1 (part by wt.) | α-Diketone*2 (part by wt.) | Peroxy Ester*3 (part by wt.) | Exposure Time (sec) | Depth of Curing (mm) | Color Glass Filter |
| --- | --- | --- | --- | --- | --- | --- |
| Example 23 | 3G 100 | KQ 1.0 | TBB 1.0 | 30 | 7.3 | None |
| Example 24 | 3G 100 | KQ 1.0 | TBB 1.0 | 40 | 4.6 | Y-43 |
| Example 25 | 3G 50 & bis-GMA 50 | PQ 0.1 & KQ 1.0 | TBB 1.0 & TAB 0.5 | 20 | 5.5 | None |
| Example 26 | 3G & bis-GMA 50 | PQ 0.1 & KQ 1.0 | TBB 1.0 & TAB 0.5 | 40 | 5.0 | Y-47 |
| Example 27 | bis-GMA 50 & UDMA 50 | KQ 2.0 | TBB 1.0 & THB 0.2 | 30 | 5.4 | None |
| Example 28 | bis-GMA 50 & UDMA 50 | KQ 2.0 | TBB 1.0 & THB 0.2 | 40 | 4.0 | Y-47 |
| Example 29 | bis-GMA 50 & HMDA 50 | AQ 0.1 & KQ 0.5 | TBB 1.0 & TOB 1.0 | 30 | 7.3 | None |
| Example 30 | bis-GMA 50 & HMDA 50 | AQ 0.1 & KQ 0.5 | TBB 1.0 & TOB 1.0 | 40 | 4.5 | Y-43 |
| Example 31 | 3G 50 & HDMP 50 | KQ 1.5 | TBB 0.5 & TCB 0.5 | 30 | 5.8 | None |
| Example 32 | 3G 50 & HDMP 50 | KQ 1.5 | TBB 0.5 & TCB 0.5 | 40 | 4.2 | Y-47 |
| Example 33 | 3G 100 | BQ 0.1 & KQ 0.7 | TBB 0.5 & TIB 0.1 | 25 | 6.5 | None |
| Example 34 | 3G 100 | BQ 0.1 & KQ 0.7 | TBB 0.5 & TIB 0.1 | 40 | 4.5 | Y-43 |

Note:
*1All of the abridged notations are the same as noted in the Note of Table 1.
*2KQ: Camphorquinone
PQ: 9,10-Phenanthrenequinone
AQ: Acenaphthenequinone
BQ: β-Naphtoquinone
*3All of the abridged notations are the same as noted in the Note of Table 1.

TABLE 5

|  | Ethylenic Unsaturated Compound (part by wt.) | Light Polymerization Initiator (part by wt.) | Exposure Time (sec) | Depth of Curing (mm) | Color Glass Filter |
| --- | --- | --- | --- | --- | --- |
| Comparative Example 4 | 3G 100 | KQ 1.0 | 40 | 0 | Y-43 |
| Comparative Example 5 | 3G 100 | KQ 1.0 & TBP* 1.0 | 40 | 0 | Y-43 |
| Comparative Example 6 | 3G 100 | KQ 1.0 | 20 | 0.2 | None |
| Comparative Example 7 | 3G 100 | KQ 1.0 & TBP* 1.0 | 30 | 0.5 | None |

Note:
*TBP: t-Butylperoxybenzoate

EXAMPLE 35

Preparation of High Polymer Surface Active Agent

Each of the copolymers (high polymer surface active agents) having the compositions as set forth in Table 6 was synthesized by an ordinary solution polymerization process while using benzene as the solvent and 2,2'-azobisisobutylonitrile as the polymerization initiator. Each copolymer was precipitated in petroleum ether to obtain a solid copolymer. The weight average molecular weights of respective copolymers were determined by the GPC method. The results are shown in Table 6.

Preparation of Paste

Each of the light polymerization initiators and the copolymers, as set forth in Table 7, was dissolved in each mixture of ethylenic unsaturated compound to prepare a solution. The solution was charged in a kneader and slowly added with fine particles of an inorganic filler, and the admixture was kneaded at atmospheric pressure for 2 hours. The admixture was kneaded under a reduced pressure of lower than 20 mmHg for additional 2 hours to be defoamed, whereby a dental composition paste of the present invention was prepared.

Test

Each of the pastes having the compositions as set forth in Table 7 was irradiated by a projector including four halogen lamps (150 watts) for a pre-set time period to obtain a cured product. The tackiness of the surface of the molded paste was observed by a finger touch test. The bending strength of each cured product was measured by the method which will be described in detail hereinbelow.

Method for the Determination of Bending Strength

A cellophane sheet was laid over a stainless steel mold, and a paste was charged and pressed on the cellophane sheet. The top face of the paste was covered by another cellophane sheet, and then a slide glass plate was put thereon under a pressure to flatten the surface so that the molded paste had even side faces. Thereafter, the slide glass plate was removed, and the paste was exposed to irradiation of lights from the top face thereof for 2 minutes to be cured sufficiently. The cured product or resin was put out of the mold, and machined to form a test piece having a length of 60 mm, a width of 10 mm and a thickness of 2.5 mm. The test piece was aged for 24 hours after the light polymerization, and then subjected to bending test. The span between the fulcra carrying the test piece was set to 50 mm, and the bending strength of the test piece was measured at a cross-head speed of 2 mm/min using a bending tester attached to an autograph. The bending strength was calculated from the following equation of:

Bending Strength $$[kg/cm^2] = \frac{3Fl}{2bd^2};$$

wherein F is the maximum stress applied to the test piece, l is the distance between the fulcra, b is the width of the test piece, and d is the thickness of the test piece.

Bending strengths of five test pieces for each cured resin were measured and the average value thereof was calculted. The results are shown in Table 7.

TABLE 6

| Copolymer | Composition | Mixing Ratio (wt %) | Weight Average Molecular Weight |
|---|---|---|---|
| A | Methoxyethyl Methacrylate | 5 | 113,000 |
|   | Methoxydiethyleneglycol Monomethacrylate | 60 | |
|   | Methyl Methacrylate | 35 | |
| B | Methoxytetraethyleneglycol Monomethacrylate | 50 | 152,000 |
|   | Methyl Methacrylate | 45 | |
|   | Ethyl Acrylate | 5 | |
| C | Methoxytetraethyleneglycol Monomethacrylate | 45 | 108,000 |
|   | Phenoxytetraethyleneglycol Monoacrylate | 5 | |
|   | Methyl Methacrylate | 50 | |
| D | Isobutoxytriethyleneglycol Monomethacrylate | 5 | 120,000 |
|   | Methoxypolyethyleneglycol Monomethacrylate (n = 9) | 25 | |
|   | Methyl Methacrylate | 70 | |

TABLE 7

| Ex. 35 Run No. | Unsaturated Compound*1 (part by weight) | Fine Particles of Inorganic Filler*2 (part by weight) | Copolymer (part by weight) | Light Polymerization Initiator*3 (part by weight) | Bending Strength (kg/cm²) | Tackiness |
|---|---|---|---|---|---|---|
| 1 | 3G 34 MPEPP 34 | S-1 30 | A 2 | TBB 0.6 BMTF 0.006 | 1110 ± 50 | No |
| 2 | 3G 30 MPEPP 30 | S-1 38 | B 2 | TBB 0.6 BMTF 0.006 | 1010 ± 80 | No |
| 3 | 3G 35 MPEPP 35 | S-1 25 | C 5 | TBB 0.6 Camphorquinone 0.06 | 1150 ± 90 | No |
| 4 | 3G 34 MPEPP 34 | S-2 30 | D 2 | TBB 0.6 Camphorquinone 0.06 | 1080 ± 50 | No |
| 5 | 3G 34 MPEPP 34 | S-2 30 | A 2 | TBB 0.6 BMTF 0.006 | 1220 ± 130 | No |

Note:
*¹3G: Triethyleneglycol Dimethacrylate
MPEPP: 2,2-Bis(4-methacryloxydiethoxyphenyl)propane
*²S-1: Silica treated with dimethyldicholorosilane and having an average particlesize of 20 millimicrons.
S-2: Silica treated with hexamethyldisilazane and having an average particle size of 15 millimicrons.
*³TBB: 3,3',4,4'-Tetra-(t-butylperoxycarbonyl)benzophenone
BMTF: 4-(4-Butoxyphenyl)-2,6-bis(4-methoxyphenyl)thiopyrylium Fluoroborate Although the present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A light curable dental paste comprising an ethylenic unsaturated compound, a light polymerization initiator, a high polymer surface active agent and fine particles of an inorganic filler, said high polymer surface active agent being a copolymer which is prepared by copolymerizing an unsaturated monomer represented by the following general formula (III) of:

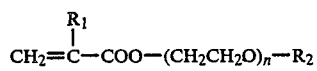

wherein $R_1$ is a hydrogen atom or a methyl group, $R_2$ is an alkyl group having 1 to 4 carbon atoms or a phenyl group, and n is an integer of 1 to 15; with an unsaturated ester copolymerizable with said monomer represented by the general formula (III), said light polymerization initiator comprising a combination of an organic peroxide and a pyrylium salt compound represented by the following general formula (I) of:

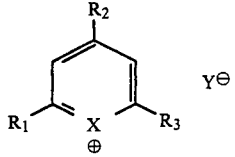

wherein $R_1$, $R_2$ and $R_3$ each represents the same or different atom or group and stands for a hydrogen atom, a halogen atom, an alkyl group, a haloalkyl group, an ethylenyl group, a styryl group, an alkoxy group, a phenyl group, a naphthyl group, an alkylphenyl group, an alkoxyphenyl group, a hydroxyphenyl group, a halophenyl group, a nitrophenyl group, an aminophenyl group, an alkylaminophenyl group, an alkylaminostyryl group, a nitro group, an amino group or a hydroxyl group, X stands for an oxygen atom or a sulfur atom and Y for an anionic functional group.

2. A composition as claimed in claim 1, wherein 0.0001 to 1 part, by weight, of said pyrylium salt compound is added to 100 parts, by weight, of said ethylenic unsaturated compound.

3. A composition as claimed in claim 1, wherein 0.001 to 10 parts, by weight, of said organic peroxide is added to 100 parts, by weight, of said ethylenic unsaturated compound.

4. A composition as claimed in claim 1, wherein said ethylenic unsaturated compound is a derivative of methacrylic acid.

5. A composition as claimed in claim 4, wherein said derivative of methacrylic acid is selected from the group consisting of triethyleneglycol dimethacrylate, hexamethyleneglycol dimethacrylate, 2,2-bis[4-(3- methacryloxy-2-hydroxypropoxy)phenyl]propane, di-2-methacryloxyethyl-2,2,4-trimethylhexamethylene dicarbamate, 1,2-bis(3-methacryloxy-2-hydroxypropoxy)ethane, tetramethylolmethane trimethacrylate, 2,2-bis(4-methacryloxyethoxyphenyl)propane, polypropyleneglycol dimethacrylate, methyl methacrylate, 2,2-bis(4-methacryloxypolyethoxyphenyl)propane and mixtures thereof.

6. A composition as claimed in claim 1, wherein said organic peroxide is an organic compound having one or more oxygen-oxygen bonds in one molecule.

7. A composition as claimed in claim 6, wherein said organic peroxide is selected from the group consisting of lauroyl peroxide, benzoyl peroxide, ditertiarybutyl-diperoxy isophthalate, 2,5-dimethyl-2,5-di(benzoylperoxy)hexane, 3,3',4,4'-tetra-(tertiarybutylperoxycarbonyl)benzophenone, tertiarybutylperoxybenzoate, tri(-tertiarybutylperoxy) trimellitate and mixtures thereof.

8. A composition as claimed in claim 1, wherein said pyrylium salt compound is selected from the group consisting of 4-(4-butoxyphenyl)-2,6-bis(4-methoxyphenyl)pyrylium fluoroborate, 4-(4-butoxyphenyl)-2,6-bis(4-methoxyphenyl)thiopyrylium fluoroborate, 2,6-bis(4-methoxyphenyl)-4-phenylthiopyrylium fluoroborate, 4-(4-butoxyphenyl)-2,6-diphenylpyrylium fluoroantimonate, 4-(4-dimethylaminophenyl)2,6-diphenylthiopyrylium perchlorate, 2,4,6-tri(4-methoxyphenyl)-thiopyrylium fluoroborate and mixtures thereof.

9. A composition as claimed in claim 1, wherein said inorganic filler is selected from the group consisting of apatite, soda-lime glass, quartz, silica, borosilicate glass, alumina, barium oxide, zirconium glass and mixtures thereof.

10. A composition as claimed in claim 1, wherein said inorganic filler comprises silica and said silica has an average particle size of from 1 to 100 millimicrons and is treated to be hydrophobic with a treating agent selected from the group consisting of dimethyldichlorosilane, hexamethyldisilazane, octyltrimethoxysilane and silicone oils.

11. A composition as claimed in claim 1, comprising 30 to 80 parts, by weight, of said ethylenic unsaturated compound, 10 to 50 parts, by weight, of said fine particles of said inorganic filler and 0.1 to 20 parts, by weight, of said copolymer.

12. A composition as claimed in claim 1, wherein said unsaturated monomer represented by the general formula [III] is selected from the group consisting of methoxyethyl acrylate, methoxyethyl methacrylate, methoxydiethyleneglycol acrylate, methoxydiethyleneglycol methacrylate, methoxytetraethyleneglycol acrylate, methoxytetraethyleneglycol methacrylate, isobutoxypolyethyleneglycol acrylate, isobutoxypolyethyleneglycol methacrylate, methoxypolyethyleneglycol acrylate, methoxypolyethyleneglycol methacrylate, phenoxypolyethyleneglycol acrylate, phenoxypolyethyleneglycol methacrylate and mixtures thereof.

13. A composition as claimed in claim 1, wherein said unsaturated ester copolymerizable with said monomer represented by the general formula [III] is selected from the group consisting of acrylic esters, methacrylic esters and mixtures thereof.

14. A composition as claimed in claim 13, wherein said unsaturated ester copolymerizable with said monomer represented by the general formula [III] is selected from the group consisting of methyl acrylate, methyl methacrylate, ethyl acrylate, ethyl methacrylate, butyl acrylate, butyl methacrylate and mixtures thereof.

15. A composition as claimed in claim 1, wherein said peroxide used in combination with said pyrylium salt compound is a polyperoxy ester containing a benzophenone group and represented by the following general formula [II] of:

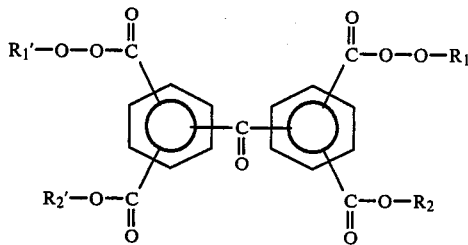

wherein $R_1$ and $R_1'$ each represents the same or different group and stands for a tertiary alkyl group having 4 to 8 carbon atoms or a tertiary aralkyl group having 9 to 12 carbon atoms and $R_2$ and $R_2'$ each represents the same or different atom or group and stands for a hydrogen atom, a tertiary alkoxy group having 4 to 8 carbon atoms or a tertiary aralkyloxy group having 9 to 12 carbon atoms.

16. A composition as claimed in claim 1, wherein said ethylenic unsaturated compound is triethyleneglycol dimethacrylate, said organic peroxide is lauroyl peroxide and said pyrylium salt compound is 4-(4-butoxyphenyl)-2,6-bis(4-methoxyphenyl)thiopyrylium fluoroborate.

* * * * *